United States Patent [19]

Yoshii et al.

[11] Patent Number: 5,211,959
[45] Date of Patent: May 18, 1993

[54] PROCESSES FOR PRODUCING SLOW-RELEASE POWDERS

[75] Inventors: Fumio Yoshii; Keizo Makuuchi; Isao Ishigaki, all of Gunma, Japan

[73] Assignee: Japan Atomic Energy Research Institute, Tokyo, Japan

[21] Appl. No.: 637,533

[22] Filed: Jan. 4, 1991

[30] Foreign Application Priority Data

Jan. 11, 1990 [JP] Japan .................................. 2-4237
Feb. 3, 1990 [JP] Japan .................................. 2-25013
May 24, 1990 [JP] Japan .................................. 2-134976
May 24, 1990 [JP] Japan .................................. 2-134977

[51] Int. Cl.$^5$ .......................... A61K 9/14; A61K 7/46; A61K 47/32; C08F 2/54
[52] U.S. Cl. ...................... 424/489; 424/501; 424/502; 424/409; 523/102; 523/122; 523/300; 522/78; 522/184; 522/186; 522/911; 522/912; 514/772.6
[58] Field of Search ............... 424/489, 501, 502, 409, 424/81; 523/300, 102, 122; 522/184, 186, 78, 911, 912; 514/772.6

[56] References Cited

U.S. PATENT DOCUMENTS

| | | | |
|---|---|---|---|
| 4,020,156 | 4/1977 | Murray et al. | 424/489 |
| 4,252,785 | 2/1981 | Isoldi | 424/409 |
| 4,404,183 | 9/1983 | Kawata et al. | 424/501 |
| 4,411,754 | 10/1983 | Kaetsu et al. | 424/81 |
| 4,652,443 | 3/1987 | Yoshida et al. | 424/81 |
| 5,043,161 | 8/1991 | Scarpelli et al. | 424/401 |

*Primary Examiner*—Thurman K. Page
*Assistant Examiner*—E. J. Webman
*Attorney, Agent, or Firm*—Banner, Birch, McKie & Beckett

[57] ABSTRACT

A process for producing a slow-release powder which permit various active ingredients such as perfumes, insect control agents, rust inhibitors, mold inhibitors and antibacterial agents to be slowly released over a prolonged time, the process comprising the steps of mixing a long-chain compound with the ingredients, mixing the resulting mixture with urea, and exposing the resulting urea adduct to radiation.

4 Claims, No Drawings

5,211,959

PROCESSES FOR PRODUCING SLOW-RELEASE POWDERS

BACKGROUND OF THE INVENTION

This invention relates to processes for producing slow-release powders. In one aspect, this invention provides a process for producing a slow-release powder by first mixing a long-chain compound with a slow-releasable substance and then mixing the resulting mixture with urea. In another aspect, the invention provides a process for producing a slow-release powder by first mixing a long-chain compound with a slow-releasable substance, then mixing the resulting mixture with urea, and finally exposing the resulting urea adduct to radiation.

Slow-release powders permit various active ingredients such as perfumes, insect control agents, rust inhibitors, mold inhibitors and antibacterial agents to be slowly released over a prolonged time, thereby expanding the application field of those substances. The use of slow-release powders has been expanding these days as an adjunct to improvements in the quality of national life.

Known clathrates (hereinafter sometimes referred to as "adducts") capable of incorporating various substances include hydroquinone, deoxycholic acid, perhydrotriphenylene and cyclodextrins. The last-mentioned cyclodextrins form clathrates in powder form that are fairly high in their ability to include substances. However, it is not easy to form slow-release powders with cyclodextrins since the steps of incorporating slow-releasable substances and drying the mixture to obtain a powder are quite time-consuming. Furthermore, compared to urea used in the present invention, cyclodextrins are low in their ability to include substances and yet they are expensive.

The present inventors conducted intensive studies in order to develop an economical technique for producing slow-release powders having longer life and, as a result, they have succeeded in attaining this objective by using a mixture of urea and a long-chain compound, which idea has not been conceived of in the light of conventional clathrates including slow-releasable substances.

SUMMARY OF THE INVENTION

The first object of the present invention is to provide an economical and safe slow-release powder. More particularly, the short life and high cost which are the two major disadvantages of conventional slow-release powders can be eliminated by incorporating a slow-releasable substance in an adduct of urea and a long-chain compound. It is well known that urea forms adducts with certain substances. However, urea mixed with a slow-releasable substance does not form an adduct with the latter and the desired slow-release powder cannot be obtained. As a result of their continued studies, the present inventors found that a slow-releasable substance could be incorporated in an adduct of urea and a long-chain compound by a two-step process comprising the steps of mixing the slow-releasable substance with the long-chain compound and mixing the resulting mixture with urea. The present invention has been accomplished on the basis of this finding.

The second object of the present invention is to provide a slow-release powder that does not contain any residual long-chain compound. The present inventors noted that long-chain compounds had two double bonds (C=C) in their molecule that rendered them highly polymerizable. The inventors therefore attempted to reduce or eliminate those long-chain compounds by polymerization. As a result of their continued studies, the inventors found that the long-chain compounds in the adducts of urea and slow-releasable substances readily polymerized by exposure to radiation. The second aspect of the present invention has been accomplished on the basis of this finding. The characteristic feature of this aspect lies in first incorporating a slow-releasable substance in an adduct of urea and a long-chain compound and then polymerizing the long-chain compound by exposure to radiation.

DETAILED DESCRIPTION OF THE INVENTION

The present invention is described below in detail.

Long-Chain Compound

While various long-chain compounds can be used in the present invention, those which have a molecular weight of at least 100 and which have functional groups attached to a molecule comprising oxyethylene or recurring methylene groups were found to be particularly effective in allowing slow-releasable substances to be incorporated into the crystal of urea. Such long-chain compounds include: higher alcohols such as hexyl alcohol [$CH_3(CH_2)_5OH$], normal octyl alcohol [$CH_3(CH_2)_7OH$], nonyl alcohol [$CH_3(CH_2)_8OH$], decyl alcohol [$CH_3(CH_2)_9OH$], undecyl alcohol [$CH_3(CH_2)_{10}OH$] and lauryl alcohol [$CH_3(CH_2)_{11}OH$]; aliphatic acids such as normal capric acid [$CH_3(CH_2)_8COOH$], caproic acid [$CH_3(CH_2)_4COOH$], lauric acid [$CH_3(CH_2)_{10}COOH$], oleic acid ($C_{18}H_{34}O_2$), linoleic acid ($C_{18}H_{32}O_2$) and stearic acid [$CH_3(CH_2)_{16}COOH$]; and polymerizable monomers such as 1,6-hexanediol diacrylate, 1,6-hexanediol monoacrylate, lauryl acrylate ($C_{15}H_{28}O_2$), stearyl acrylate ($CH_2=CHCOOC_{18}H_{23}$) and caprolactone modified 2-hydroxyethyl acrylate ($C_{11}H_{18}O_5$). Any other long-chain compounds can be used to have various substances incorporated into urea adducts as long as they have a comparatively small degree of branching, have molecular weights of at least 100 and if they are capable of forming adducts with urea.

Various slow-releasable substances can be used in the present invention and typical examples are described below.

Natural and Synthetic Perfumes

Both natural and synthetic perfumes can be used in the present invention and natural perfumes may be either animal or plant derived such as lavender oil, citronella oil, rose oil, lemon oil and jasmine oil. Various synthetic perfumes can also be used and they include, for example, acetophenone ($C_8H_8O$), anisic aldehyde ($C_8H_8O_2$), anisole ($C_7H_8O$), undecylenic aldehyde ($C_{11}H_{20}O$), isoamyl formate ($C_6H_{12}O_2$), geranyl formate ($C_{11}H_{16}O_2$), isoamyl acetate ($C_7H_{14}O_2$), dimethylbenzylcarbinyl acetate ($C_{12}H_{16}O_2$), vanillin ($C_8H_8O_3$), isoamyl propionate ($C_8H_{16}O_2$), ethyl propionate ($C_5H_{10}O_2$), paramethyl acetophenone ($C_9H_{10}O$) and isoamyl butyrate ($C_9H_{18}O_2$). Other perfumes can also be used if they are capable of forming adducts with urea in the presence of long-chain compounds.

Insect Control and Insect Killing Agents

Insect control agents that can be used in the present invention are those compounds which have insect control and killing effects, as exemplified by p-dichlorobenzene, o-dichlorobenzene and dimethyl phthalate. Other insect control and killing agents may of course be employed if they are capable of forming adducts with urea in the presence of long-chain compounds.

Rust Inhibitors

Rust inhibitors that can be used in the present invention include aliphatic acids and metal soaps. Rust inhibiting oils can also be used and they include spindle oils, turbine oils and cylinder oils. Any other rust inhibitors and rust inhibiting oils can be used as long as they are capable of forming adducts with urea in the presence of long-chain compounds.

Mold Inhibitors and Bactericides

The mold inhibitors that can be used in the present invention include those which have bacteriostatic and bactericidal effects and may be exemplified by toluene, 5-ethoxy-3-trichloromethyl-1,2,4-thiadiazole, 1,4-dichloro-2,5-dimethoxybenzene, 2,6-dichloro-4-tetraaniline and zinc ethylenebisdithiocarbonate. Other mold inhibitors having bacteriostatic or bactericidal effects can also be used as long as they are capable of forming adducts with urea in the presence of long-chain compounds.

The two processes for producing slow-release powders according to the present invention are described below. The first process comprises the steps of mixing a long-chain compound with a slow-releasable substance and mixing the resulting mixture with urea. The second process comprises the steps mixing a long-chain compound with a slow-releasable substance, mixing the resulting mixture with urea, and exposing the resulting urea adduct to radiation.

In either process, the ratio of the long-chain compound to the slow-releasable substance ranges from 1:0.1 to 1:10 on a weight basis. The exact value of this ratio will vary with the molecular weight of the specific slow-releasable substance used and slow-releasable substances having higher molecular weights will be used in smaller proportions. If the proportion of the long-chain compound is too low, incorporation of the slow-releasable substance will become difficult to accomplish. If, on the other hand, the proportion of the long-chain compound is excessive, the concentration of the slow-releasable substance in the urea adduct will be too low to produce a slow-release powder having satisfactory performance.

The ratio of urea to the long-chain compound ranges from 1:5 to 1:15, preferably from 1:8 to 1:11, on a molar basis. If the proportion of urea is too low, incorporation of the slow-releasable substance becomes difficult to accomplish. If, on the other hand, the proportion of urea is excessive, an increasing amount of urea will remain unreacted to form an adduct with the long-chain compound, which is by no means economical.

No special method of addition is required to perform the first step of mixing the slow-releasable substance with the long-chain compound. If the slow-releasable substance is liquid, the long-chain compound need be dissolved in said substance. If the slow-releasable substance is solid, it may be heated or otherwise treated to increase its solubility and is then dissolved in the long-chain compound.

The second step of mixing the (liquid) mixture of the slow-releasable substance and the long-chain compound with urea can also be performed without requiring any special technique and said liquid may be gently mixed with urea under agitation as it is sprayed with the liquid. When mixed under agitation, urea will first absorb the liquid to form a paste and increase in volume. When the paste sample is left to stand, it gradually decreases in volume to turn to a freely flowing powder, or the intended slow-release powder of the present invention. The second step will be completed within a period of from about 2 to 20 hours. The agitation is effected at a temperature of 20°-80° C., preferably at 30°-60° C. If the temperature for agitation exceeds 80° C., the urea adduct will decompose. The atmosphere for agitation is not limited in any particular way but the use of a closed vessel is preferred in order to avoid dissipation of the slow-releasable substance.

The slow-release powder obtained by the process of the present invention may be formulated by common techniques in the art and various slow-release powder product can be produced by any known methods.

The polymerization reaction initiated by exposure to radiation is the third step of the process according to the second aspect of the present invention is carried out in order to render the long-chain compound in the slow-release powder harmless by radiation-initiated polymerization. In this third step, the adduct of urea and the long-chain compound which has the slow-releasable substance incorporated therein is polymerized by irradiation in a closed vessel. If the proportion of the slow-releasable substance in the urea adduct is comparatively low, the long-chain compound is very reactive as to polymerize merely by irradiation. If, on the other hand, the concentration of the slow-releasable substance in the urea adduct is high, the long-chain compound is not sufficiently reactive to have the intended reaction proceed to the fullest extent. In this case, the urea adduct is heated to generate an active species, which is utilized to polymerize the long-chain compound. Radiations that can be used to perform the third step include gamma-rays, electron beams, X-rays and any other kinds of radiations that may be used on an industrial basis. The dose of radiation ranges from 5 to 100 kGy, preferably from 20 to 60 kGy. If the dose of radiation is too small, the long-chain compound may not be completely polymerized. If the dose of radiation is excessive, the slow-releasable substance may be decomposed by radiation. If necessary, the adduct exposed to radiation may be heated at 40°-70° C., preferably at 50° C. If the heating temperature exceeds 70° C., the adduct can potentially decompose. No special method is required to implement irradiation, but irradiation in an inert atmosphere using a closed vessel is preferred.

The present invention is described below in greater detail with reference to examples and comparative examples.

EXAMPLE 1

A slow-release powder of an insect control agent, o-dichlorobenzene (o-DCB) was prepared. When used alone, o-DCB will not form a clathrate with urea but it can be incorporated into a urea adduct in the presence of a long-chain compound.

When 4 g of urea was mixed under agitation with a liquid mixture of 1.4 g of oleic acid as a long-chain compound and 0.48 g of o-DCB, the mixture first took on a paste form but upon standing, the paste turned to a free-flowing powder in about 10 hours, which was a slow-release powder incorporating the insect control agent. A slow-release test was conducted by measuring the amount of residual o-DCB incorporated in the powder at predetermined time intervals of heating at 50° C. As a comparison, a mixture of o-DCB (0.48 g) and urea (4 g) that was formed in the absence of a long-chain compound was heated at 50° C. and the amount of residual o-DCB was measured at predetermined time intervals. In the comparison, the mixture had the liquid o-DCB adhering to the solid crystal of urea. The long-chain compound was not released at all from the slow-release powder and only o-DCB was slowly released from the powder. The test results are shown in the following table, from which one can clearly see that in the presence of the long-chain compound, a slow-release powder was successfully obtained that had o-DCB incorporated into the urea adduct. It took as many as two days for substantially all of the o-DCB to be released from the slow-release powder.

| Time (hr) | Example 1 Slow-release powder | Comparative Example 1 Mixture of urea and o-DCB |
|---|---|---|
| 4 | 83% | 70% |
| 8 | 65 | 43 |
| 24 | 21 | 0 |

EXAMPLE 2

A slow-release powder of a mold inhibitor, toluene, was prepared. As in Example 1, toluene used alone did not form an adduct with urea but when urea was added to a mixture of toluene with a long-chain compound, a slow-release compound incorporating toluene could be formed. Stated more specifically, 4 g of hexanediol diacrylate as urea was added to a liquid mixture of 1.47 g of a long-chain compound and 0.6 g of toluene and by agitation and subsequent standing for about 10 hours, a free-flowing slow-release powder incorporating toluene formed. As a comparison, a mixture of 0.6 g of toluene and 4 g of urea was formed in the absence of a long-chain compound and the amount of residual toluene was measured at predetermined time intervals of heating at 50° C. The test results are shown in the following table, from which one can clearly see that a slow-release powder having toluene incorporated in a urea adduct could be obtained in the presence of a long-chain compound.

| Time (hr) | Example 2 Slow-release powder | Comparative Example 2 Mixture of urea and toluene |
|---|---|---|
| 4 | 70% | 56% |
| 8 | 58 | 42 |
| 24 | 26 | 0 |

EXAMPLE 3

A slow-release powder was prepared using a synthetic perfume giving off the fragrance of chewing gum and having a molecular weight of ca. 100. As in Example 1, the perfume used alone did not form an adduct with urea but in the presence of hexanediol diacrylate as a long-chain compound, the perfume formed an adduct with urea, thereby producing a slow-release powder of the perfume. Stated more specifically, 8.0 g of urea was added to a liquid mixture of 0.82 g of the perfume and 1.85 g of the long-chain compound and by agitation and subsequent standing for about 5 hours, the mixture which was initially in a paste form gradually turned to a slow-release powder incorporating the perfume. Upon standing at room temperature, the powder retained the fragrance of the perfume for at least 3 months.

EXAMPLE 4

A slow-release powder was prepared using a perfume giving off the fragrance of pine resin and having a molecular weight of ca. 130. In this example, too, the perfume used. alone did not form an adduct with urea but in the presence of hexanediol diacrylate as a long-chain compound, the perfume formed an adduct with urea. Stated more specifically, 8 g of urea was added to a liquid mixture of 1.85 g of a long-chain compound and 0.82 g of the perfume and by agitation and subsequent standing for about 5 hours, the mixture which was initially in a paste form gradually turned to a slow-release powder incorporating the perfume. The resulting urea adduct gave off the fragrance of pine resin that lasted for at least 3 months.

The results of Examples 1–4 clearly show that a slow-release powder having a slow-releasable substance incorporated into a urea adduct could be formed in the presence of a long-chain compound.

EXAMPLE 5

A slow-release powder was prepared using a synthetic perfume, isobutyl acetate (IBA). When used alone, IBA will not form a clathrate with urea but it can be incorporated into a urea adduct in the presence of oleic acid as a long-chain compound.

When 6 g of urea was mixed under agitation with a liquid mixture of 1.89 g of oleic acid and 0.78 g of IBA, the mixture first took on a slurry form but upon standing for ca. 5 hours, the slurry turned to a free-flowing powder, which was a slow-release powder incorporating the perfume IBA. A slow-release test was conducted by gravimetric measurements of the amount of residual IBA incorporated in the powder at predetermined time intervals of standing at room temperature. As a comparison, a mixture of IBA (0.78 g) and urea (6 g) that was formed in the absence of oleic acid was left to stand at room temperature and the amount of residual IBA was measured at predetermined time intervals. In the comparison, the mixture had the perfume IBA adhering to the solid crystal of urea. Oleic acid was not released at all from the slow-release powder and only IBA was slowly released from the powder. The test results are shown in the following table, from which one can clearly see that in the presence of oleic acid, a slow-release powder was successfully obtained that had IBA incorporated into the urea adduct.

| Time (hr) | Example Slow-release powder | Comparative Example 5 Mixture of urea and IBA |
|---|---|---|
| 5 | 87.7% | 83.4% |
| 27 | 51.1 | 29.9 |
| 45 | 30.2 | 0 |
| 67 | 16.6 | |

EXAMPLE 6

Using lauryl acrylate as a long-chain compound, a urea adduct having a synthetic perfume IBA incorporated into the urea crystal was prepared as in Example 5 and the resulting urea adduct was subjected to a slow-release test as in Example 5. Lauryl acrylate was used in an amount of 1.61 g. When the liquid mixture of lauryl acrylate and IBA was mixed with urea under agitation, the mixture which was initially in the form of slurry gradually turned to a powder upon standing for ca. 10 hours. The test results clearly show that in the presence of lauryl acrylate, IBA was incorporated into the urea adduct to form a slow-release powder.

| Time (hr) | Example 6 Slow-release powder | Comparative Example 6 Mixture of urea and IBA |
| --- | --- | --- |
| 5 | 83.1% | 89.6% |
| 27 | 39.4 | 29.0 |
| 45 | 22.2 | 0 |
| 67 | 20.1 | |

EXAMPLE 7

Using caprolactone-modified 2-hydroxyl acrylate (trade name, Alonix 154) as a long-chain compound, a synthetic perfume IBA was incorporated into a urea adduct. The preparation of the urea adduct and the testing of its ability to release IBA were conducted as in Example 5. Alonix 154 was used in an amount of 1.54 g. As in Example 5, the mixture of urea with the liquid mixture of Alonix 154 and IBA was initially in a slurry form but as it was agitated and left to stand over time, the mixture turned into a slow-release powder having IBA incorporated into the urea adduct. The slow release of IBA demonstrates its incorporation in the urea adduct. There was no detectable release of Alonix 154 from the powder.

| Time (hr) | Example 7 Slow-release powder | Comparative Example 7 Mixture of urea and IBA |
| --- | --- | --- |
| 5 | 88.7% | 89.6% |
| 27 | 55.5 | 29.9 |
| 45 | 35.8 | 0 |
| 67 | 27.5 | |

EXAMPLE 8

A slow-release powder was prepared using a synthetic perfume, isobutyl acetate (IBA), that was incorporated in an adduct of urea and a polymer. When used alone, IBA will not form an adduct with urea but it can be incorporated into a urea adduct in the presence of hexanediol diacrylate as a long-chain compound.

A long-chain compound (1.47 g) and IBA (0.75 g) were mixed and the resulting mixture was sprayed on 5.6 g of urea. The mixture was then left to stand overnight at 25° C. to form the powder of a urea adduct having IBA incorporated in the long-chain compound. The adduct was irradiated with gamma-rays for a dose of 50 kGy and heated at 50° C. for 15 minutes to polymerize the long-chain monomer in the adduct, whereby a slow-release powder was obtained that consisted of the urea adduct having the synthetic perfume incorporated in the adduct of urea and the polymer of the long-chain compound. The thus obtained slow-release powder was tested for its ability to slowly release the synthetic perfume. As a comparison, 1.47 g of the long-chain compound and 0.75 g of IBA were mixed and the resulting mixture was sprayed on 5.6 g of urea and, after leaving the mixture to stand overnight at 25° C., the resulting urea adduct having IBA incorporated in the long-chain compound was checked for its ability to slowly release IBA without irradiation with gamma-rays. The slow release of IBA from the urea adduct was determined by gravimetric measurements of IBA release at predetermined time intervals of standing in a 50-ml open weighing bottle at 25° C. The results of measurements indicate the amounts of residual perfume in the adduct. In the tests, the long-chain compound was not at all found to be released from the adduct. The test results are shown in the following table, from which one can clearly see that the slow releasability of IBA from the unirradiated adduct was completely retained even after the adduct was irradiated with gamma-rays to polymerize the long-chain compound in the adduct. Thus, the adduct of urea and long-chain compound which incorporated the synthetic perfume turned to a slow-release powder of urea and polymer upon exposure to radiation.

| Time (hr) | Example 8 After irradiation | Comparative Example 8 Before irradiation |
| --- | --- | --- |
| 8 | 79.0% | 77.0% |
| 24 | 59.7 | 56.7 |
| 48 | 28.5 | 28.7 |
| 67 | 25.4 | 23.4 |

EXAMPLE 9

A slow-release powder was prepared from an insect control agent, o-dichlorobenzene (o-DCB) that was incorporated into an adduct of urea and a polymer. Like the IBA used in Example 8, o-DCB when used alone did not form an adduct with urea but in the presence of hexanediol diacrylate as a long-chain compound, o-DCB could be incorporated into a urea adduct. To state more specifically, 4 g of urea was added to a liquid mixture of a long-chain compound (1.47 g) and o-DCB (0.48 g) and by thorough stirring and subsequent standing overnight, the mixture turned into a free-flowing powder of the adduct of urea and the long-chain compound. When this powder was irradiated with gamma-rays for a dose of 60 kGy, the long-chain compound in the urea adduct polymerized to yield a product having the insect control agent incorporated in the adduct of urea and the polymer of the long-chain compound. As a comparison, an unirradiated adduct of urea and a long-chain compound was prepared that had the insect control agent incorporated therein. A slow-release test was conducted by determining the amount of residual o-DCB incorporated into the adduct at predetermined time intervals of heating at 50° C. in an open weighing bottle. The test results are shown in the following table, from which one can clearly see that the slow-release speed of the long-chain compound in the irradiated adduct was substantially the same irrespective of whether said compound was radiation-polymerized or not. It took 48 hours for substantially all of the o-DCB to be released from the adduct. Hence, the long-chain compound polymerized by irradiation successfully yielded a powder of the urea-polymer adduct which had the insect control agent incorporated therein.

| Time (hr) | Example 9 After irradiation | Comparative Example 9 Before irradiation |
| --- | --- | --- |
| 6 | 76.1% | 73.2% |
| 22 | 27.3 | 38.3 |

-continued

| Time (hr) | Example 9 After irradiation | Comparative Example 9 Before irradiation |
| --- | --- | --- |
| 30 | 16.3 | 23.6 |

EXAMPLE 10

A slow-release powder was prepared using an adduct of urea and a polymer which had a synthetic perfume incorporated therein that gave off the fragrance of chewing gum and that had a molecular weight of ca. 100. In this example, too, the synthetic perfume used alone did not form an adduct with urea but in the presence of hexanediol diacrylate as a long-chain compound, the perfume successfully formed an adduct with urea to form a slow-release powder. When the long-chain compound was polymerized by exposure to radiation, a more harmless slow-release powder was obtained that had the synthetic perfume incorporated in the adduct of urea and the polymer of the long-chain compound. To state more specifically, 8.0 g of urea was added to a liquid mixture of 1.85 g of the long-chain compound and 0.82 g of the perfume and by agitation and subsequent standing for ca. 5 hours, the mixture which was initially in a paste form gradually turned into a powder, thus yielding an adduct of urea and the long-chain compound that had the perfume incorporated therein. When this adduct was irradiated with gamma-rays for a dose of 50 kGy, the long-chain compound in the adduct polymerized to produce a slow-release powder having the synthetic perfume incorporated in the adduct of urea and the polymer of the long-chain compound. This slow-release powder permitted the contained perfume to sustain its fragrance for a period of at least 3 months when it is left at room temperature. It was therefore clear that the slow releasability of the perfume remained the same even when the long-chain compound in the urea adduct was polymerized by irradiation.

EXAMPLE 11

A slow-release powder was prepared using an adduct of urea and a polymer which had a perfume incorporated therein that gave off the fragrance of pine resin and that had a molecular weight of ca. 130. In this example, too, the perfume used alone did not form an adduct with urea but in the presence of hexanediol diacrylate as a long-chain compound, the perfume successfully formed an adduct with urea. To render the long-chain compound harmless, the adduct of urea and the long-chain compound harmless, the adduct of urea and the long-chain compound which had the pine resin perfume incorporated therein was exposed to radiation. To state more specifically, 8 g of urea was added to a liquid mixture of 1.85 g of the long-chain compound and 0.82 g of the perfume and by agitation and subsequent standing for ca. 5 hours, the mixture which was initially in a paste form gradually turned into a powder, thus yielding an adduct of urea and the long-chain compound that had the perfume incorporated therein. When this adduct was irradiated with gamma-rays for a dose of 50 kGy, the long-chain compound in the adduct polymerized to produce a slow-release powder having the perfume incorporated in the adduct of urea and the polymer of the long-chain compound. This slow-release powder permitted the contained perfume to sustain its fragrance of pine resin for a period of at least 3 months.

EXAMPLE 12

A slow-release powder was prepared using an adduct of urea and a polymer which had a synthetic perfume, isobutyl acetate (IBA) incorporated therein. When used alone, IBA will not form an adduct with urea but it can be incorporated into a urea adduct in the presence of lauryl acrylate.

Lauryl acrylate (1.61 g) and IBA (0.78 g) were mixed and the resulting liquid mixture was sprayed on 6 g of urea. The mixture was then left to stand at room temperature, whereupon a slow-release powder was obtained that had IBA incorporated in a urea adduct. The adduct was irradiated with gamma-rays for a dose of 100 kGy to polymerize the lauryl acrylate in the adduct, whereby a slow-release powder was obtained from the adduct having the synthetic perfume incorporated in the adduct of urea and the polymer of lauryl acrylate. The thus obtained slow-release powder was tested for its ability to slowly release the synthetic perfume. As a comparison, 1.61 g of lauryl acrylate and 0.78 g of IBA were mixed and the resulting liquid mixture was sprayed on 6 g of urea and, after leaving the mixture to stand overnight at room temperature, the resulting urea adduct having IBA incorporated in lauryl acrylate was checked for its ability to slowly release IBA without irradiation with gamma-rays. The slow-release test was conducted in the same way as in Example 8. In the test, lauryl acrylate was not at all found to be released from the adduct. The test results are shown in the following table, from which one can clearly see that the slow releasability of IBA from the unirradiated adduct was completely retained even after the adduct was irradiated with gamma-rays to polymerize lauryl acrylate in the adduct. Thus, the adduct of urea and lauryl acrylate which incorporated the synthetic perfume turned to a slow-release powder of urea and polymer upon exposure to radiation.

| Time (hr) | Example 12 After irradiation | Comparative Example 12 Before irradiation |
| --- | --- | --- |
| 20 | 64.8% | 58.25 |
| 42 | 40.6 | 32.0 |
| 72 | 25.1 | 25.0 |

EXAMPLE 13

Using 2-hydroxyethyl acrylate monomer [$CH_2=CHCOOCH_2CH_2OCO(CH_2)_5OH$], a synthetic perfume, isobutyl acetate (IBA), was incorporated into a urea adduct to produce a slow-release powder.

A liquid mixture of 2-hydroxyethyl acrylate monomer (1.54 g) and IBA (0.78 g) was sprayed on 6 g of urea and, after thorough agitation and subsequent standing at room temperature, the resulting mixture was left to stand overnight, whereupon a slow-release powder was obtained that had IBA incorporated in the monomer in a urea adduct. The adduct was irradiated with gamma-rays for a dose of 100 kGy to polymerize the monomer, whereby a slow-release powder was obtained from the adduct having the perfume incorporated in the adduct of a urea and the polymer. The thus obtained slow-release powder was tested for its ability to slowly release the perfume. As a comparison, a liquid mixture of 2-hydroxyethyl acrylate monomer (1.54 g) and IBA (0.78 g) was sprayed on urea and the resulting mixture was thoroughly agitated. After leaving the mixture to stand overnight, the resulting urea adduct having IBA incorporated in the monomer was checked for its ability to slowly release IBA without irradiation with gamma-rays. The slow-release test was conducted in the same way as in Example 8. In the test, the monomer was not at all found to be released from the adduct. The test results are shown in the following table, from which one can clearly see that the slow releasability of IBA from the unirradiated adduct did not vary greatly even when the adduct was irradiated with gamma-rays to polymerize the monomer in the adduct. Thus, the adduct of urea and monomer which incorporated the synthetic perfume turned to a slow-release powder of urea and polymer upon exposure to radiation.

| Time (hr) | Example 13 After irradiation | Comparative Example 13 Before irradiation |
|---|---|---|
| 20 | 61.7% | 71.9% |
| 42 | 35.0 | 40.6 |
| 72 | 25.2 | 28.9 |

What is claimed is:

1. A process for producing a slow release powder by the steps of:
   first mixing a long-chain compound and a slow-releasable substance, wherein the weight ratio of said long-chain compound to said slow-releasable substance ranges from 1:0.1 to 1:10; and
   then mixing the resulting mixture with urea at a temperature ranging from 20° to 80° C., wherein the molar ratio of said urea to said long-chain compound ranges from 1:5 to 1:15,
   wherein said long-chain compound has a molecular weight of at least 100, said long-chain compound facilitating the incorporation of said slow-releasable substance into said urea to form a urea adduct, wherein said long chain compound is selected from the group consisting of hexyl alcohol, n-octyl alcohol, nonyl alcohol, decyl alcohol, undecyl alcohol, lauryl alcohol, n-capric acid, caproic acid, lauric acid, oleic acid, linoleic acid, stearic acid, 1,6-hexanediol diacrylate, 1,6-hexanediol monoacrylate, lauryl acrylate, stearyl acrylate and caprolactone modified 2-hydroxyethyl acrylate, and
   wherein the slow-releasable substance is selected from the group consisting of a natural perfume, a synthetic perfume, an insect control agent, an insect killing agent, a rust inhibitor, a mold inhibitor and an antibacterial agent.

2. A process for producing a slow release powder by the steps of:
   mixing a long chain compound with a slow-releasable substance, wherein the weight ratio of said long-chain compound to said slow-releasable substance ranges from 1:0.1 to 1:10;
   mixing the resulting mixture with urea at a temperature ranging from 20° to 80° C., wherein the molar ratio of said urea to said long-chain compound ranges from 1:5 to 1:15; and
   exposing the resulting urea adduct to radiation, wherein the dose of radiation ranges from 5 to 100 kGy,
   wherein said long-chain compound has a molecular weight of at least 100 and is polymerizable upon exposure to radiation, said long-chain compound facilitating the incorporation of said slow-releasable substance into said urea to form a urea adduct, wherein said long chain compound is selected from the group consisting of oleic acid, linoleic acid, 1,6-hexanediol diacrylate, 1,6-hexanediol monoacrylate, lauryl acrylate, stearyl acrylate and caprolactone modified 2-hydroxyethyl acrylate, and
   wherein the slow-releasable substance is selected from the group consisting of a natural perfume, a synthetic perfume, an insect control agent, an insect killing agent, a rust inhibitor, a mold inhibitor and an antibacterial agent.

3. A process according to claim 1 or 2 wherein said long-chain compound is a mixture of two or more compounds.

4. A process according to claim 2 wherein said radiation is gamma-rays, electron beams or X-rays.

* * * * *